United States Patent [19]

Dawson

[11] Patent Number: 5,401,656
[45] Date of Patent: Mar. 28, 1995

[54] USE OF HUMAN IMMORTALIZED ENDOTHELIAL CELLS TO ISOLATE AND PROPAGATE *EHRLICHIA CHAFFEENSIS* AND *EHRLICHIA CANIS*

[75] Inventor: Jacqueline E. Dawson, Atlanta, Ga.

[73] Assignee: United States of America, Washington, D.C.

[21] Appl. No.: 968,821

[22] Filed: Oct. 30, 1992

Related U.S. Application Data

[63] Continuation-in-part of Ser. No. 518,182, May 3, 1990, Pat. No. 5,192,679, and a continuation-in-part of Ser. No. 687,526, Apr. 18, 1991, abandoned.

[51] Int. Cl.$^6$ .................... C12N 5/00; C12N 5/06; C12N 5/08
[52] U.S. Cl. ..................... 435/243; 435/240.1; 435/240.2; 435/240.21; 435/252.1; 435/260
[58] Field of Search ............ 435/240.2, 240.21, 240.1, 435/260, 252.1, 243

[56] References Cited

PUBLICATIONS

Lawley, et al in Ryan (Ed.) Endothelial Cells vol. III pp. 229–240 CRC Press, (1987).
Fishbein, et al. JAMA 257:3100–3104, (1987).
Kelly, et al. Abstracts of the Annual Meeting of the American Society for Microbiology, (1985) 3–7 Mar. 1985 p. 171 Abstract No. J 17.
Anderson, B. E., J. E. Dawson, D. C. Jones, and K. H. Wilson. 1991. Ehrlichia chaffeensis, a new species associated with human ehrlichiosis. J. Clin. Microbiol. 29:2838–2842.
Dawson, J. E., B. E. Anderson, D. B. Fishbein, J. L. Sanchez, C. S. Goldsmith, K. H. Wilson, and C. W. Duntley. 1991. Isolation and characterization of an Ehrlichia sp. from a patient diagnosed with human ehrlichiosis. J. Clin. Microbiol. 29:2741–2745.
Dumler, J. S., P. Brouqui, J. Aronson, J. P. Taylor, and D. H. Walker. 1991. Identification of Ehrlichia in human tissue. [letter] N. Eng. J. Med. 325:1109–1110.
Walker, D. H. 1989. Rocky Mountain spotted fever: a disease in need of microbiological concern. Clin. Microbiol. Rev. 2:227–240.

*Primary Examiner*—Michael G. Wityshyn
*Assistant Examiner*—Jane Williams
*Attorney, Agent, or Firm*—Needle & Rosenberg

[57] ABSTRACT

This invention provides a purified immortalized human endothelial cell infected with *Ehrlichia chaffeensis* or *Ehrlichia canis*. Also provided is a method of simultaneously screening a sample from a human subject for the presence of *E. chaffeensis* and *Rickettsia rickettsii* comprising contacting the sample with immortalized human endothelial cells under conditions which allow infection of the cells and detecting the presence of infection, the presence of infection indicating the presence of *E. chaffeensis* and/or *R. rickettsii*. The invention also provides a method of screening a sample from a human subject for the presence of *E. chaffeensis* comprising contacting the sample with endothelial cells under conditions which allow infection of the cells by *E. chaffeensis* and detecting the presence of infection by *E. chaffeensis*, the presence of infection by *E. chaffeensis* indicating the presence of *E. chaffeensis* in the sample. Finally, the invention provides a method of culturing *E. chaffeensis* or *E. canis* comprising contacting *E. chaffeensis* or *E. canis* with immortalized human endothelial cells under conditions which allow the propagation of *E. chaffeensis* or *E. canis*.

5 Claims, No Drawings

USE OF HUMAN IMMORTALIZED ENDOTHELIAL CELLS TO ISOLATE AND PROPAGATE *EHRLICHIA CHAFFEENSIS* AND *EHRLICHIA CANIS*

This invention is a continuation-in-part of U.S. Ser. No. 07/518,182, filed May 3, 1990, now U.S. Pat. No. 5,192,672, and U.S. Ser. No. 07/687,526, filed April 18, 1991, now abandoned, the contents of which are hereby incorporated by reference.

BACKGROUND OF THE INVENTION

1. Field of the Invention

This invention is directed to cells and methods for screening and propagating *Ehrlichi chaffeensis* and *Ehrlichia canis*.

2. Background Art

Human ehrlichiosis and Rocky Mountain spotted fever are both tick-borne diseases that cause significant morbidity and mortality in the United States (12, 14, 17, 19). Approximately 260 cases of human ehrlichiosis, including 5 fatalities, have been serologically confirmed in the United States since 1986 (3). In addition, one case each has been reported in Portugal (16) and Mali, Africa (18). In contrast, state health departments reported 649 cases of Rocky Mountain spotted fever in 1990 (4). Rocky Mountain spotted fever is a reportable disease, human ehrlichiosis is not. Therefore, reliable estimates of the number of human ehrlichiosis cases are not available.

*Ehrlichia chaffeensis*, the etiologic agent of human ehrlichiosis, was first isolated in 1990 (2, 8). Prior to the isolation of *E. chaffeensis*, human ehrlichiosis was diagnosed based upon a fourfold change in antibody titer to *E. canis* (6, 7). *E. canis*, the etiologic agent of canine ehrlichiosis, is closely related to *E. chaffeensis* and was originally suspected of being the etiologic agent of human ehrlichiosis (15).

Human ehrlichiosis is generally characterized by fever, malaise, headache, myalgia, rigor, nausea/vomiting, arthralgia, rash, and cough (10, 11). Many of the same clinical signs and symptoms characterize an infection with *Rickettsia rickettsii*, etiologic agent of Rocky Mountain spotted fever (19). Although the characteristic rash of Rocky Mountain spotted fever, on the palms of the hands and the soles of the feet, may help to distinguish this disease from human ehrlichiosis, the rash is often not observed during the first few days after onset of illness (19). If a febrile illness after tick exposure is reported, neither disease can be immediately ruled out.

*R. rickettsii* are short rods 0.3–0.5 μm in diameter and 0.8–2.0 μm in length. Growth occurs in the cytoplasm, sometimes in the nucleus, of certain vertebrate and arthropod cells. Ultrathin sections viewed by electron microscopy reveal typical envelopes consisting of cell wall and cytoplasmic membranes and internal structures analogous to the ribosomes and DNA strands identified in other microorganisms.

*E. chaffeensis* are often pleomorphic, coccoid to ellipsoidal. Individual organisms are approximately 0.5 μm in diameter, and morulae range in size up to 4.0 μm in diameter. These organisms occur in membrane-bound vacuoles in the cytoplasm of leukocytes, forming inclusions that contain variable numbers of organisms. Members of the tribe Ehrlichieae have distinct ribosomes and DNA strands. Clumps of ribosomes are homogenously distributed in the cytoplasm rather than marginated beneath the cytoplasmic membrane. Compared with those of the rickettsiae or ordinary bacteria, the DNA and ribosomes in members of the tribe Ehrlichieae are more loosely packed in the cytoplasm.

*R. rickettsii* organisms enter by tick bite, spread via the lymphatics and blood stream to all parts of the body including skin, brain, lungs, kidneys, heart, liver, spleen, pancreas, and gastrointestinal tract (19). In each tissue, the rickettsiae proliferate within endothelial cells and vascular smooth muscle cells (19). *R. rickettsii* can be cultivated in a variety of cell lines including Vero cells, L cells, primary chicken embryo fibroblasts, WI-38, and HeLa. However, *R. rickettsii* must be maintained for several weeks, because the incubation period of rickettsiae can be long and growth with new isolates may be sparse for a week or longer (19).

Little is known about the pathogenesis of *E. chaffeensis*. However, in one fatal case, Ehrlichia sp. organisms were demonstrated by immunohistology in the splenic cords and sinuses, splenic periarteriolar lymphoid sheaths, hepatic sinusoids, lymph nodes, lung microvasculature, bone marrow, kidney, and epicardium (9). Ehrlichia sp. morulae were most frequently detected in large mononuclear cells and infrequently in small lymphocyte-like cells (9).

Since the quantity of an acute blood specimen received is often limited and successful isolation is directly related to the volume of blood inoculated, there is a need for one cell line that would support the growth of both *E. chaffeensis* and *R. rickettsii*. This invention satisfies this need.

SUMMARY OF THE INVENTION

This invention provides a purified immortalized human endothelial cell infected with *Ehrlichia chaffeensis* or *Ehrlichia canis*. Also provided is a method of simultaneously screening a sample from a human subject for the presence of *E. chaffeensis* and *Rickettsia rickettsii* comprising contacting the sample with immortalized human endothelial cells under conditions which allow infection of the cells and detecting the presence of infection, the presence of infection indicating the presence of *E. chaffeensis* and/or *R. rickettsii*. The invention also provides a method of screening a sample from a human subject for the presence of *E. chaffeensis* comprising contacting the sample with endothelial cells under conditions which allow infection of the cells by *E. chaffeensis* and detecting the presence of infection by *E. chaffeensis*, the presence of infection by *E. chaffeensis* indicating the presence of *E. chaffeensis* in the sample. Finally, the invention provides a method of culturing *E. chaffeensis* or *E. canis* comprising contacting *E. chaffeensis* or *E. canis* with immortalized human endothelial cells under conditions which allow the propagation of *E. chaffeensis* or *E. canis*.

DETAILED DESCRIPTION OF THE INVENTION

This invention provides the first showing that *E. chaffeensis* and *E. canis* can be efficiently propagated in an endothelial cell line. Thus, the invention provides a purified immortalized human endothelial cell infected with *E. chaffeensis* or *E. canis*.

The following cell lines did not support the growth of *E. canis*; CF2Th, A-72, MDCK, VERO, P388D1, CHO, Hu/Ha863, Hu/Ha937, HUT 78, MH-1 and HL-60.

"Purified" as used herein means separated from at least some of the proteins and other impurities associated with a naturally-occurring cell. Since the invention is directed to "infected" endothelial cells, only those endothelial cells which can be infected with E. canis or E. chaffeensis and support efficient propagation are within the scope of the invention. Other endothelial cells which can support efficient propagation of E. canis and E. chaffeensis can be screened for by the methods taught in the Examples.

In a preferred embodiment, the endothelial cell is an immortalized human microvascular endothelial cell. The cell set forth in the Examples is HMEC-1. HMEC-1 (ATCC No. CRL 10636) was deposited with the American Type Culture Collection, 12301 Parklawn Drive, Rockville, Md. 20852 U.S.A. on Jan. 8, 1991.

This invention also provides a method of simultaneously screening a sample from a human subject for the presence of E. chaffeensis and R. rickettsii. The method comprises contacting the sample with immortalized human endothelial cells under conditions which allow infection of the cells and detecting the presence of infection, the presence of infection indicating the presence of E. chaffeensis and/or R. rickettsii. If desired, the method can further comprise determining whether the infection is E. chaffeensis or R. rickettsii. Thus, infection by E. chaffeensis or R. rickettsii can be distinguished and their associated diseases diagnosed. Presently preferred cells are immortalized human microvascular endothelial cells, especially HMEC-1.

Many methods exist to determine the presence of infection. For example, the presence of infection can be determined by direct immunofluorescence. Other methods to detect infection include staining, e.g., Giemsa, Wright/Giemsa or Diff-Quik®. Acridine Orange can also be utilized to stain the organisms.

Likewise, the invention also provides a method of culturing E. chaffeensis or E. canis. The method comprises comprising contacting E. chaffeensis or E. canis with immortalized human endothelial cells under conditions which allow the propagation of E. chaffeensis or E. canis. As above, immortalized human microvascular endothelial cells can be utilized, especially HMEC-1.

Conditions which allow infection and propagation of the cells are set forth in the Examples. Infection was carried out with serum-free endothelial basal medium (EBM) media. However, isolation can be accomplished with complete EBM with fetal bovine serum (FBS). Propagation conditions can utilize complete EBM (Clonetics, San Diego, Calif.) supplemented with 5 ml of 200 mm L-glutamine (Gibco, Grand Island, N.Y.), hydrocortisone 2 $\mu$m, epidermal growth factor 5 mg/ml and 15% heat-inactivated fetal bovine serum. Given the teachings provided herein, routine modifications can be made to growth and propagation conditions. Isolation can be accomplished in between 1 and 60 days. Once isolated, the organisms can be propagated indefinitely.

The invention also provides a method of screening a sample from a human subject for the presence of E. chaffeensis. The method comprises contacting the sample with endothelial cells under conditions which allow infection of the cells by E. chaffeensis and detecting the presence of infection by E. chaffeensis, the presence of infection by E. chaffeensis indicating the presence of E. chaffeensis in the sample.

The invention demonstrates that both canine and human pathogens grow in the human endothelial cell line. Why the canine pathogen grew more efficiently in the HMEC-1 cells (day 11) is an enigma. With time, however, both Ehrlichia spp. grew almost equivalently in the HMEC-1 cells. E. chaffeensis-infected HMEC-1 cells reached a maximum of 75% cell infectivity (day 14), while the E. canis-infected HMEC-1 cells were 60% infected on the same day. It is possible that the cells would have become more heavily infected if the cultures had not been split.

The results with R. rickettsii demonstrate that this organism can be grown easily in HMEC-1 or DH82 cells. Therefore, for the primary isolation of R. rickettsii the HMEC-1 cell line seems to be as efficient as the DH82 cells.

Although both the DH82 and HMEC-1 cells can be used for growth of all three organisms, the pathogenesis of these organisms in these two very different cell lines remains unknown. Propagation of Ehrlichia sp. in a human cell line can be more analogous to in vivo pathogenesis.

EXAMPLES

Materials and Methods

Propagation of HMEC-1 cells. HMEC-1 cells were propagated in 75 $cm^2$ cell culture flasks, with 0.2 u filter caps (Costar, Cambridge, Mass.), at 37° C. with 5% supplemental $CO_2$. Culture medium for actively dividing uninfected cells consisted of endothelial basal medium (EBM) (Clonetics, San Diego, Calif.) supplemented with 5 ml of 200 mM L-glutamine (Gibco, Grand Island, N.Y.); hydrocortisone 2 $\mu$m; epidermal growth factor, 5 ng/ml; and 15% heat-inactivated fetal bovine serum (FBS). Medium was changed every 7 days, at which time the cells were split 1:2.

Cultivation of Ehrlichia spp. in DH82 cells. E. chaffeensis and E. canis organisms were cultured in the continuous canine macrophage cell line DH82. Cell monolayers were propagated in 150-$cm^2$ plastic cell culture flasks at 37° C. without supplemental $CO_2$. Culture medium consisted of minimal essential medium supplemented with 12% heat-inactivated FBS and 1% L-glutamine (200 mM). Medium was changed every 48 to 72 hours.

Ehrlichia Inoculum

When 60% of the DH82 cells became infected with Ehrlichia sp., as determined by the results of a previously described direct immunofluorescence procedure (7, 13), 1×150 $cm^2$ culture of each agent was harvested by decanting the old medium, adding 10 ml of EBM and removing the monolayer with a cell scraper. Each cell suspension was centrifuged at 250×g for 10 minutes, resuspended in 4 ml of serum-free EBM and dounce homogenized (100 strokes), thereby liberating the organisms from host cells. This suspension was centrifuged at 100×g for 10 minutes to remove any host cell debris.

The number of E. canis or E. chaffeensis per milliliter was calculated as described (5). Briefly, 10 $\mu$l of 1:100 dilution of each suspension was placed on the grid area of a hemacytometer. After drying, the organisms were stained, not with acridine orange, as previously described, but by the direct immunofluorescence procedure (7, 13). An ultraviolet microscope was used to calculate the number of E. canis and E. chaffeensis organisms contained in each suspension ($3.5 \times 10^6$ organisms per milliliter).

The 4-ml suspension of E. chaffeensis organisms was equally divided into 2×75 cm² cultures of HMEC-1 cells. The same procedure was repeated with the E. canis organisms liberated from host cells. Serum-free medium was changed every 7 days in the cultures with a static HMEC-1 monolayer.

Monitoring Ehrlichia sp. Infection

The percentage of cells infected with Ehrlichia sp. was monitored by direct immunofluorescence on days 4, 7, 11, 14, 18, 21, 25, 28, 35, and 42. When the number of infected cells reached 60%, supernatant was discarded and replaced with complete EBM supplemented with 15% FBS. The monolayers were scraped off both the infected flask and a 75 $cm^2$ culture flask of uninfected cells. The cell suspensions were combined and then divided equally into the two original flasks. The addition of an equal number of uninfected cells allowed the Ehrlichia sp. to spread to other HMEC-1 cells.

*R. rickettsii* Inoculum

One 2-ml vial of *E. rickettsii*-infected Vero cells (Sheila Smith strain) was thawed rapidly and then dounce homogenized (50 strokes). Seven ml of EBM was added, and the suspension was centrifuged at 900×g for 15 minutes. Equal volumes of the suspension were added to 1×75 $cm^2$ culture of HMEC-1 cells and 1×75 $cm^2$ culture of DH82 cells.

Monitoring *R. rickettsii* Infection

The percentage of infected cells was monitored by direct immunofluorescence on days 5, 8, and 14. Both the *E. rickettsii*-infected HMEC-1 cell cultures and the *E. rickettsii*-infected DH82 cell cultures were split 1:2 by adding an equal number of the respective uninfected cells (as described above for the Ehrlichia-infected HMEC-1 cultures).

Result

Ehrlichia spp.-infected HMEC-1 cells. Both the *E. chaffeensis* and *E. canis* HMEC-1 cells were infected by day 4 after inoculation. By day 11 after inoculation, both canis-infected HMEC-1 cell cultures were 70% infected, while the *E. chaffeensis*-infected HMEC-1 cell cultures were only 40%–45% infected.

The *E. chaffeensis* cultures reached a maximum of 70%–75% infected cells on day 14. Both cultures were split 1:2 and even though supplemental uninfected HMEC-1 cells were added, the number of infected cells declined to approximately 1% on day 18. From day 18 through 42, the number of *E. chaffeensis*-infected HMEC-1 cells never rose above 2%. The cultures were discontinued on day 42.

The *E. canis* cultures reached a maximum of 70% infected HMEC-1 cells on day 11. Both cultures were split 1:2. Three days later, all four cultures were between 50%–60% infected. This contrasts strongly with the decline of the *E. chaffeensis* cultures after a 1:2 split, using the same cell line. However, from day 18 through 42, the number of *E. canis*-infected HMEC-1 cells never rose above 10%. The cultures were discontinued on day 42.

*R. rickettsii*-Infected HMEC-1 Cells

The HMEC-1 *E. rickettsii*-infected culture was 90% infected by day 5 after inoculation. The culture was split 1:2 (only one flask was retained). By day 8, the HMEC-1 cells were again 90% infected. The culture was split 1:2 for the second time and by day 14 was again 90% infected.

*R. rickettsii*-Infected DH82 Cells

The DH82 *R. rickettsi*-infected culture was 100% infected by day 5 after inoculation. The culture was split 1:2 (only one flask was retained). By day 8, the DH82 cells were again 100% infected. The culture was split 1:2 for the second time and by day 14 was 90% infected. Both the HMEC-1 and DH82 *R. rickettsii*-infected cultures were discontinued on day 14 after being split two times, equivalent to the Ehrlichia spp.-infected cultures.

Throughout this application various publications are referenced. The full citation of the publications is listed immediately prior to the claims. The disclosures of these publications in their entireties are hereby incorporated by reference into this application in order to more fully describe the state of the art to which this invention pertains.

The preceding examples are intended to illustrate but not limit the invention. While they are typical of those that might be used, other procedures known to those skilled in the art may be alternatively employed.

TABLE 1

| | Percent of *E. chaffeensis* or *E. canis*-infected HMEC-1 cells on days 4-42 after inoculation. | | | |
|---|---|---|---|---|
| Days after inoculation | % infected *E. chaffeensis* cells culture #1 | % infected *E. chaffeensis* cells Culture #2 | % infected *E. canis* cells Culture #1 | % infected *E. canis* cells Culture #2 |
| 4 | 2 | 5 | 10 | 15 |
| 7 | 20 | 15 | 50 | 50 |
| 11 | 45 | 40 | 70* | 70* |
| 14 | 70* | 75* | 50/60* | 50/60* |
| 18 | <1/1 | <1/<1 | 10/1/10 | 5/10/10 |
| 21 | <1/<1 | <1/<1 | 50/5/10+ | 10/10/10+ |
| 25 | <1/<1 | 1/1 | 50/5 | 10/10 |
| 28 | 1/1 | <1/2 | 30/10 | 15/15 |
| 35 | 2/<1 | <1/2 | 10/5 | <1/5 |
| 42 | <1/0 | 0/<1 | 0/0 | 0/<1 |

*Culture split 1:2.
+ = discontinued

REFERENCES

1. Ades E. W., F. Candal, V. George, D. Bosse, S. Summers, R. Swerlick, and T. J. Lawley. Establishment of an immortalized human microvascular endothelial cell line: retention of normal morphologic, phenotypic, and functional characteristics. J. Invest. Dermatol., Dec. 1992.
2. Anderson, B. E., J. E. Dawson, D. C. Jones, and K. H. Wilson. 1991. *Ehrlichia chaffeensis*, a new species associated with human ehrlichiosis. J. Clin. Microbiol. 29:2838–2842.
3. Centers for Disease Control. 1990. Rocky Mountain spotted fever and human ehrlichiosis—United States, 1989. Morbid. Mortal. Weekly Rep. 39:281–284.
4. Centers for Disease Control. 1991. Rocky Mountain spotted fever—United States, 1990. Morbid. Mortal. Weekly Rep. 40:451–453, 459.
5. Dawson, J. E., I. Abeygunawardena, C. J. Holland, M. M. Buese, and M. Ristic. 1988. Susceptibility of cats to infection with *Ehrlichia risticii*, causative agent of equine monocytic ehrlichiosis. Am. J. Vet. Res. 49:2096–2100.
6. Dawson, J. E, D. B. Fishbein, T. R. Eng, M. A. Redus, and N. R. Greene. 1990. Diagnosis of human ehrlichiosis with the indirect fluorescent antibody test: kinetics and specificity. J. Infect. Dis. 162:91-95.
7. Dawson, J. E, Y. Rikihisa, S. A. Ewing, and D. B. Fishbein. 1991. Serologic diagnosis of human ehrlichiosis using two *Ehrlichia canis* isolates. J. Infect. Dis. 163:91-95.
8. Dawson, J. E, B. E. Anderson, D. B. Fishbein, J. L. Sanchez, C. S. Goldsmith, K. H. Wilson, and C. W. Duntley. 1991. Isolation and characterization of an Ehrlichia sp. from a patient diagnosed with human ehrlichiosis. J. Clin. Microbiol. 29:2741-2745.
9. Dumler, J. S., P. Brougui, J. Aronson, J. P. Taylor, and D. H. Walker. 1991. Identification of Ehrlichia in human tissue. [letter]N. Eng. J. Med. 325:1109-1110.
10. Eng, T. R., J. R. Harkess, D. B. Fishbein, J. E. Dawson, C. N. Greene, M. A. Redus, and F. T. Satalowich. 1990. Epidemiologic, clinical and laboratory findings of human ehrlichiosis in the United States, 1988. J. Am. Med. Assoc. 264:2251-2258.
11. Fishbein, D. B., A. Kemp, J. E. Dawson, N. R. Greene, M. A. Redus, and D. H. Fields. 1989. Human ehrlichiosis: prospective active surveillance in febrile hospitalizd patients. J. Infect. Dis. 160:803-809.
12. Fishbein, D. B., and J. E. Dawson. 1991. Ehrlichiae. In A. Balows, W. J. Hausler, K. L. Herrmann, H. D. Isenberg, H. J. Shadomy (eds.) Manual of clinical microbiology. 5th ed. American Society of Microbiology, Washington, D.C.
13. Hebert, G. A., B. Pittman, R. M. Mckinney, and W. B. Cherry. 1972. The preparation and physiochemical characterization of fluorescent antibody reagents. Centers for Disease Control, Atlanta.
14. Helmick, C. G., K. W. Bernard, and L. J. D'Angelo. 1984. Rocky Mountain spotted fever: clinical, laboratory, and epidemiological features of 262 cases. J. Infect. Dis. 150:480-488.
15. Maeda, K., N. Markowitz, R. C. Hawley, M. Ristic, D. Cox, and J. E. McDade. 1987. Human infection with *Ehrlichia canis,* a leukocytic rickettsia. N. Engl. J. Med. 316:853-856.
16. Morais, J. D., J. E. Dawson, C. Greene, A. R. Filipe, L. C. Galhardas, and F. Bacellar. 1991. First European case of ehrlichiosis. The Lancet. 338:633-634.
17. Petersen, L. R., L. A. Sawyer, D. B. Fishbein, P. W. Kelley, R. J. Thomas, L. A. Magnarelli, M. Redus, and J. E. Dawson. 1989. An outbreak of ehrlichiosis in members of an army reserve unit exposed to ticks. J. Infect. Dis. 159:562-568.
18. Uhaa, I. J., J. D. Maclean, C. R. Greene, and D. B. Fishbein. 1992. A case of human ehrlichiosis acquired in Mali: clinical and laboratory findings. Am. J. Trop. Med. Hyg. 46:161-164.
19. Walker, D. H. 1989. Rocky Mountain spotted fever: a disease in need of microbiological concern. Clin. Microbiol. Rev. 2: 227-240.

What is claimed is:

1. A purified immortalized human microvascular endothelial cell infected with a member selected from the group consisting of *Ehrlichia chaffeensis* and *Ehrlichia canis*.

2. The cell of claim 1, wherein the cell is HMEC-1 (ATCC No. CRL 10636).

3. The cell of claim 1, wherein the human microvascular endothelial cell is infected with *Ehrlichia chaffeensis*.

4. The cell of claim 1, wherein the human microvascular endothelial cell is infected with *Ehrlichia canis*.

5. A purified immortalized human microvascular endothelial cell designated HMEC-1 (ATCC No. CRL 10636) infected with a member selected from the group consisting of *Ehrlichia chaffeensis* and *Ehrlichia canis*.

* * * * *

UNITED STATES PATENT AND TRADEMARK OFFICE
CERTIFICATE OF CORRECTION

PATENT NO. : 5,401,656
DATED : Mar. 28, 1995
INVENTOR(S) : Jacqueline E. Dawson

It is certified that error appears in the above-indentified patent and that said Letters Patent is hereby corrected as shown below:

In column 1, line 16, delete "*Ehrlichi*" and insert therefor --*Ehrlichia*--. In column 5, lines 22, 33, 34 and 65 delete "*E. rickettsii*" and insert therefor --*R. rickettsii*--.

Signed and Sealed this

Seventh Day of November, 1995

Attest:

BRUCE LEHMAN

Attesting Officer

Commissioner of Patents and Trademarks